United States Patent
Suryanarayanan et al.

(10) Patent No.: US 7,466,790 B2
(45) Date of Patent: Dec. 16, 2008

(54) SYSTEMS AND METHODS FOR IMPROVING A RESOLUTION OF AN IMAGE

(75) Inventors: Srikanth Suryanarayanan, Karnataka (IN); Paul Edgar Licato, Wauwatosa, WI (US); Yogisha Mallya, Bangalore (IN); Tara Janen Mahan, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/366,093

(22) Filed: Mar. 2, 2006

(65) Prior Publication Data

US 2007/0206719 A1 Sep. 6, 2007

(51) Int. Cl.
*A61B 6/03* (2006.01)
*H05G 1/60* (2006.01)

(52) U.S. Cl. .......................................................... 378/4
(58) Field of Classification Search ...................... 378/4, 378/15, 8, 901, 62; 382/131; 600/425
See application file for complete search history.

(56) References Cited

U.S. PATENT DOCUMENTS

| | | | | |
|---|---|---|---|---|
| 5,355,309 A | * | 10/1994 | Eberhard et al. | 378/15 |
| 5,457,724 A | * | 10/1995 | Toth | 378/4 |
| 5,611,026 A | * | 3/1997 | Eberhard et al. | 345/419 |
| 5,878,102 A | | 3/1999 | Kalvin | |
| 6,301,498 B1 | | 10/2001 | Greenberg et al. | |
| 6,324,243 B1 | * | 11/2001 | Edic et al. | 378/4 |
| 6,396,897 B1 | | 5/2002 | Ebrahimifard et al. | |
| 6,504,892 B1 | * | 1/2003 | Ning | 378/4 |
| 6,549,607 B1 | | 4/2003 | Webber | |
| 6,768,782 B1 | * | 7/2004 | Hsieh et al. | 378/8 |
| 6,823,204 B2 | * | 11/2004 | Grass et al. | 600/407 |
| 6,834,096 B2 | * | 12/2004 | Launay et al. | 378/8 |
| 6,850,586 B2 | * | 2/2005 | Cahill | 378/8 |
| 7,103,136 B2 | * | 9/2006 | Claus et al. | 378/4 |
| 2004/0101179 A1 | * | 5/2004 | Suryanarayanan et al. | 382/128 |
| 2005/0135558 A1 | * | 6/2005 | Claus et al. | 378/42 |
| 2005/0259871 A1 | * | 11/2005 | Li et al. | 382/173 |
| 2006/0061570 A1 | * | 3/2006 | Cheryauka et al. | 345/424 |
| 2007/0181813 A1 | * | 8/2007 | DiBianca et al. | 250/363.08 |

* cited by examiner

*Primary Examiner*—Allen C. Ho
(74) *Attorney, Agent, or Firm*—Armstrong Teasdale LLP (57) ABSTRACT

A method for improving a resolution of an image is provided. The method includes reconstructing an image of an initial portion of an object at an initial resolution, and reconstructing an additional portion of the object at an additional resolution.

20 Claims, 6 Drawing Sheets

SYSTEMS AND METHODS FOR IMPROVING A RESOLUTION OF AN IMAGE

BACKGROUND OF THE INVENTION

This invention relates generally to imaging systems and more particularly to, systems and methods for improving a resolution of an image.

An imaging system includes a source that emits signals including, but not limited to, x-ray, radio frequency, or sonar signals, and the signals are directed toward a subject, such as a patient, to be imaged. The emitted signals and the interposed subject interact to produce a response that is received by one or more detectors. The imaging system then processes the detected response signals to generate an image of the subject. For example, in computed tomography (CT) imaging, an x-ray source projects a fan-shaped beam which is collimated to lie within an X-Y plane of a Cartesian coordinate system and generally referred to as the "imaging plane". The x-ray beam passes through the subject being imaged. The beam, after being attenuated by the subject, impinges upon an array of radiation detectors. The intensity of the attenuated beam radiation received at the detector array is dependent upon the attenuation of the x-ray beam by the subject. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the subject to be imaged so that the angle at which the x-ray beam intersects the subject constantly changes. A group of x-ray attenuation measurements, i.e., projection data, from the detector array at one gantry angle is referred to as a "view". A "scan" of the subject includes a set of views made at different gantry angles, or view angles, during one revolution of the x-ray source and detector. In an axial scan, the projection data is processed to construct an image that corresponds to a two-dimensional slice taken through the subject.

One method for reconstructing an image from a set of projection data is referred to in the art as the filtered back projection technique. The filtered backprojection technique converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the subject is translated along a z-axis while the data for the prescribed number of slices is acquired. Such a system generates a single helix from a one-fan-beam helical scan. The helix mapped out by the fan beam yields projection data from which images in each prescribed slice may be reconstructed.

Typically, a CT scan is acquired at a single field of view, which accounts for a wide part of an anatomy of the subject. As a result, an entire volume including the wide part is imaged and viewed at the same resolution. In certain instances the resolution is lower than that needed for an anatomical region and hence the ability to resolve fine structures is compromised. For example, in head and neck cases, a CT angiogram display field-of-view (DFOV) parameter is set to accommodate the wide part of anatomy in the scan, which are the shoulders. This DFOV setting is used to reconstruct a volume of the head. However, proximal to the shoulders, the width of the neck is much smaller and the DFOV reconstruction reduces an in-plane resolution in the neck. The lower in-plane resolution in the neck is further compounded by a small size of a plurality of objects of interest, such as, a plurality of vertebral arteries. At a large DFOV setting, such as 34 centimeters (cm), a width of one of the vertebral arteries in a plurality of axial planes is less than five pixels. Anatomical analysis reveals that 10% of the normal population present a smaller right vertebral artery compared to a left vertebral artery that is ipsilateral to the heart. With the right vertebral artery running through a bright cortical bone of a cervical transverse process, a boundary of the right vertebral artery is buried in partial volume. At a plurality of critical locations, such as the boundary, separating a foreground object, such as one of the vertebral arteries that is 5 pixels wide, without excursion into a neighboring object, such as a bone, or background becomes difficult. Another anatomical region that presents a similar challenge is a plurality of peripherals, such as arms and legs, of the subject. The arms and legs are also scanned at a wide FOV corresponding to an abdomen of the subject. Peripheral arteries of the subject are typically less than 2-3 millimeters (mm) in diameter and span a few voxels after reconstruction.

BRIEF DESCRIPTION OF THE INVENTION

In one aspect, a method for improving a resolution of an image is provided. The method includes reconstructing an image of an initial portion of an object at an initial resolution, and reconstructing an additional portion of the object at an additional resolution.

In another aspect, a controller is provided. The controller is configured to reconstruct an image of an initial portion of an object at an initial resolution, and reconstruct an additional portion of the object at an additional resolution.

In yet another aspect, an imaging system is provided. The imaging system includes a source configured to generate a beam, a detector array configured to detect the beam, and a controller. The controller is configured to reconstruct an image of an initial portion of an object at an initial resolution, and reconstruct an additional portion of the object at an additional resolution.

DETAILED DESCRIPTION OF THE INVENTION

Figure 1:
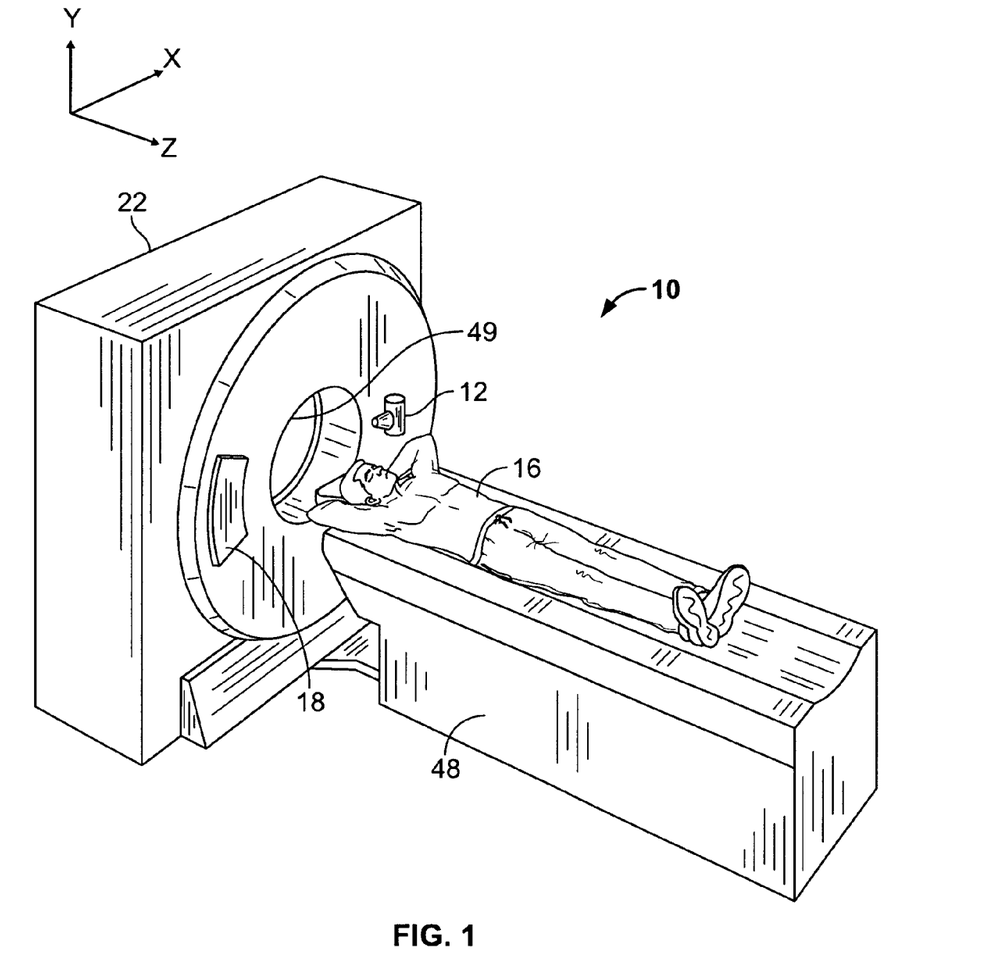
FIG. 1 is an isometric view of an embodiment of a computed tomography (CT) imaging system.
Figure 2:
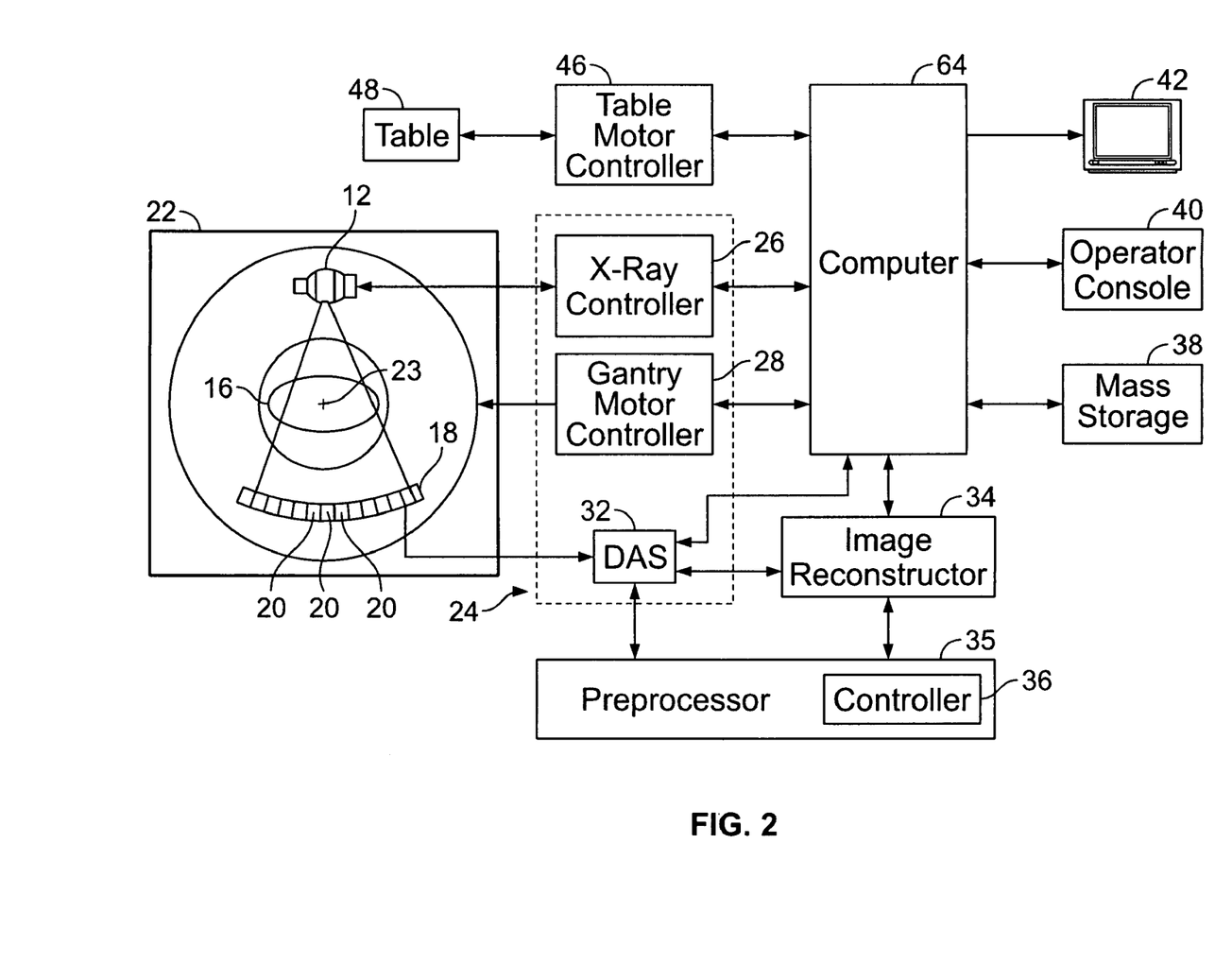
FIG. 2 is a block diagram of the CT system of FIG. 1.

FIGS. 1 and 2 illustrate an embodiment of a computed tomography (CT) imaging system 10. CT imaging system 10 includes a gantry 22 and is a "third generation"CT system. In an alternative embodiment, CT system 10 may be an energy integrating, a photon counting (PC), or a photon energy discriminating (ED) CT detector system. Gantry 22 has an x-ray source 12 that projects a beam of x-rays toward a detector array 18. The x-ray pass through a subject 16, such as a patient, to generate attenuated x-rays. Subject 16 lies along a z-axis. A height of subject 16 is parallel to the z-axis. Detector array 18 is formed by a plurality of detector elements 20 which together sense the attenuated x-rays. A row of detector array 18 is located along an x-axis and a column of detector array 18 is located along a z-axis. In an alternative embodiment, each detector element 20 of detector array 18 may be a photon energy integrating detector, a photon counting, or a photon energy discriminating detector. Each detector element 20 produces an electrical signal that represents an intensity of the attenuated x-rays. During a scan to acquire projection data, gantry 22 and components mounted on gantry 22 rotate about a center of rotation 23.

Rotation of gantry 22 and an operation of x-ray source 12 are governed by a control mechanism 24 of CT system 10. Control mechanism 24 includes an x-ray controller 26 that provides power and timing signals to x-ray source 12 and a gantry motor controller 28 that controls a rotational speed and position of gantry 22. A data acquisition system (DAS) 32 in control mechanism 24 samples and digitizes the projection data from detector elements 20 and converts the projection data to sampled and digitized projection data for subsequent processing.

A pre-processor 35 including a controller 36 receives sampled and digitized projection data from DAS 32 to pre-process the sampled and digitized projection data. In one embodiment, pre-processing includes, but is not limited to, an offset correction, a primary speed correction, a reference channel correction, and an air-calibration. As used herein, the term controller is not limited to just those integrated circuits referred to in the art as a controller, but broadly refers to a processor, a microprocessor, a microcontroller, a programmable logic controller, an application specific integrated circuit, and another programmable circuit, and these terms are used interchangeably herein. Pre-processor 35 pre-processes the sampled and digitized projection data to generate pre-processed projection data.

An image reconstructor 34 receives the pre-processed projection data from pre-processor 35 and performs image reconstruction, such as, filtered backprojection (FBP), iterative maximum likelihood expectation maximization (ML-EM), maximum a posteriori iterative coordinative descent (MAP-ICD), or algebraic reconstruction technique (ART), to generate a CT image. The CT image is applied as an input to a computer 64 which stores the CT image in a mass storage device 38. As used herein, each of the terms computer and image reconstructor is not limited to just those integrated circuits referred to in the art as a computer, but broadly refers to a processor, a microcontroller, a controller, a programmable logic controller, an application specific integrated circuit, and another programmable circuit, and these terms are used interchangeably herein. X-ray controller 26 adjusts a tube current within x-ray source 12 based on a quality of the CT image.

Computer 64 also receives commands and scanning parameters from a user, such as an operator, via a console 40 that has a user interface device. A display 42, such as a cathode ray tube monitor, allows a user, such as an operator, to observe the CT image and other data from computer 64. The commands and scanning parameters are used by computer 64 to provide control signals and information to DAS 32, x-ray controller 26, and gantry motor controller 28. In addition, computer 64 operates a table motor controller 46 which controls a motorized table 48 to position and translate subject 16 within gantry 22. Particularly, table motor controller 46 adjusts table 48 to move portions of subject 16 and center subject 16 in a gantry opening 49.

In an alternative embodiment, a high frequency electromagnetic energy projection source configured to project high frequency electromagnetic energy toward subject 16 may be used instead of x-ray source 12. A detector array disposed within a gantry and configured to detect the high frequency electromagnetic energy may also be used instead of detector array 18.

Also as used herein, reconstruction of an image is not intended to exclude embodiments of the systems and methods for filtering a measurement of a density of an object in which data representing an image is generated but a viewable image is not. Many embodiments of the systems and methods for filtering a measurement of a density of an object generate or are configured to generate at least one viewable image.

Figure 3:
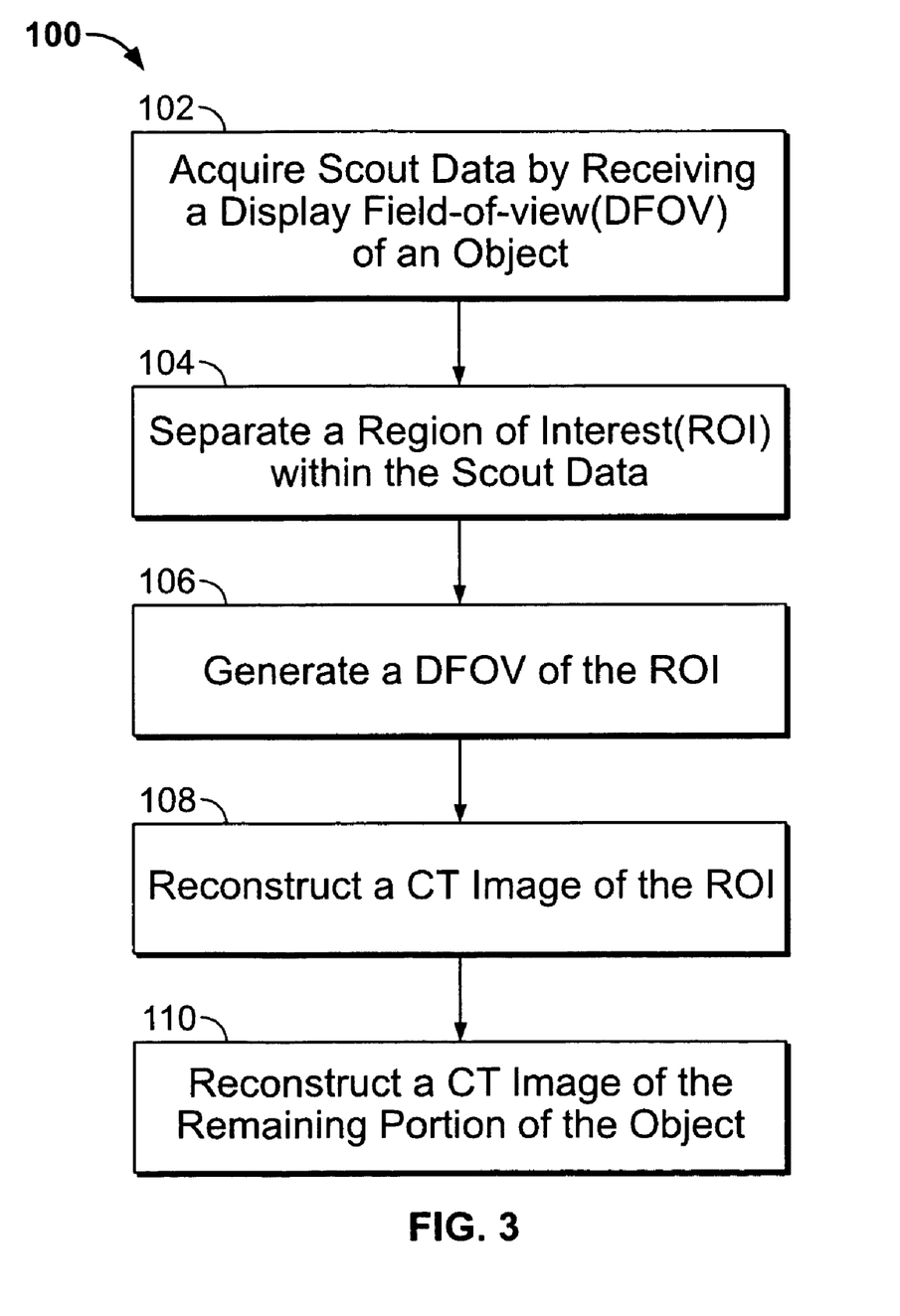
FIG. 3 is a flowchart of an embodiment of a method for improving a resolution of an image.
Figure 4:
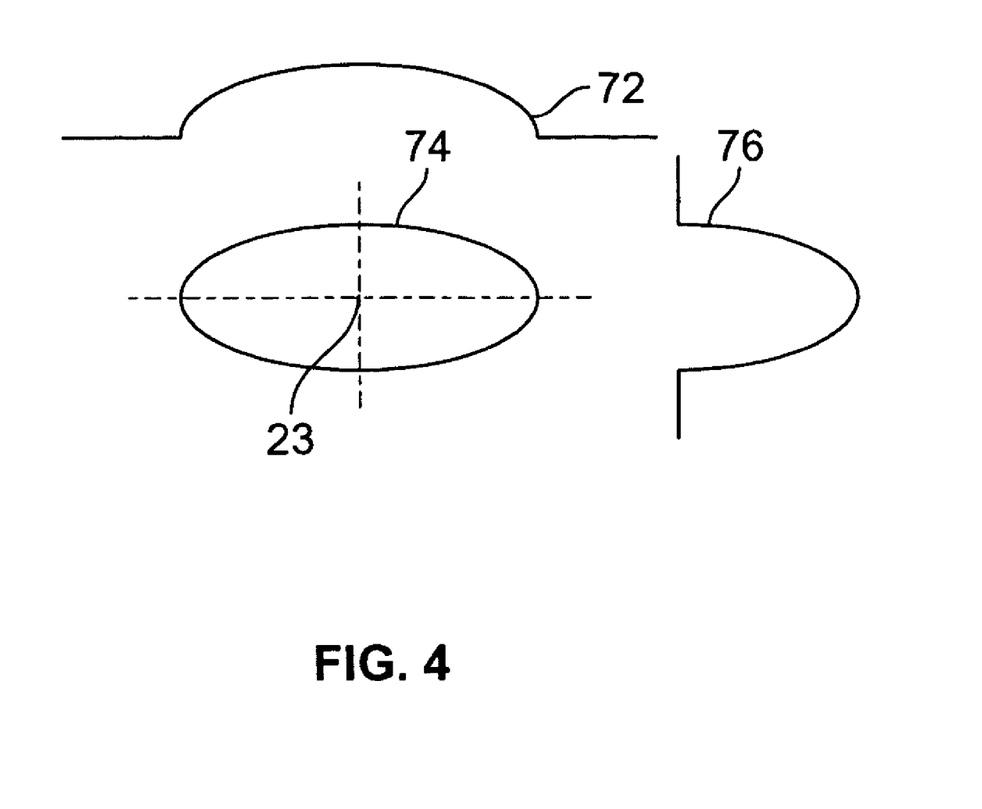
FIG. 4 is a diagram illustrating a method for acquiring scout data.

FIG. 3 is a flowchart of an embodiment of a method 100 for improving a resolution of an image. Method 100 is performed by computer 64 and image reconstructor 34. In an alternative embodiment, method 100 is performed by a single controller, Computer 64 acquires scout data. The scout data is acquired at two orthogonal scout data views, shown in FIG. 4, including a first scout data view generated by scanning an object 74 at a gantry angle of zero degrees and a second scout data view generated by scanning at a gantry angle of ninety degrees. Examples of the object 74 include a shoulder, a heart, and a vertebra of subject 16. The scout data includes a first scout data set 72 acquired at the first scout data view and a second scout data set 76 acquired at the second scout data view. Alternatively, Computer 64 acquires axial projection data. The axial projection data is acquired by performing an axial scan of along a single point along a z-axis substantially parallel to subject 16.

Referring back to FIG. 3, computer 64 acquires 102 the scout data, or alternatively the axial projection data, having a high in-plane resolution, such as from and including 0.2 millimeter (mm) to 0.4 mm, by receiving a display field-of-view (DFOV) of object 74 within subject 16. The DFOV of the object 74 has a low value, such as from and including 10 centimeters (cms) to 20 cms. The DFOV of the object 74 is input as a parameter by the user into console 40. Alternatively, computer 64 acquires the scout data or alternatively the axial projection data having a low in-plane resolution, such as from and including 0.4 mm to 0.8 mm, by receiving the DFOV of the object 74 having a high value, such as from and including 20 cms to 40 cms. Computer 64 acquires the scout data or alternatively the axial projection data of the object 74.

Computer 64 executes a partition algorithm to separate 104 a region of interest (ROI), such as a vessel of subject 16, a head of subject 16, an artery of subject 16, a vertebral artery of subject 16, a coronary artery of subject 16, an artery within a head of subject 16, a neck of subject 16, an arm of subject 16, or a leg of subject 16, within the scout data or alternatively within the axial projection data. Computer 64 executes the partition algorithm by determining an extent of the ROI within the object 74. The extent of the ROI can be determined from a shape and/or a size of the ROI. For example, computer 64 distinguishes a shape of an artery, a vessel, a head, or a neck, within the scout data or alternatively within the axial projection data. The shape of the ROI is pre-stored within mass storage device 38 by the user via console 40. As another example, computer 64 distinguishes a size of a vessel, an artery, a head, or a neck, within the scout data or alternatively the axial projection data. The size of the ROI is pre-stored within mass storage device 38 by the user via console 40. As yet another example, computer 64 distinguishes the size and/or the shape of the ROI from a structure of the remaining portion of the object 74. The structure of the remaining portion within the object 74 is pre-stored within mass storage device 38 by the user via console 40. The remaining portion within the object 74 excludes the ROI of the object 74.

Computer 64 generates 106 a DFOV of the ROI based on the DFOV of the object 74. For example, upon determining that the DFOV of the object 74 has the low value, computer 64 generates the high value as the DFOV of the ROI. As another example, upon determining that the DFOV of the object 74 has the high value, computer 64 generates the low value as the DFOV of the ROI.

Computer 64 transmits the DFOVs of the object 74 and of the ROI to image reconstructor 34. CT imaging system 10 performs a scan of the object 74 to generate the pre-processed projection data. Image reconstructor 34 receives the pre-processed projection data of the object 74 from pre-processor 35. Image reconstructor 34 reconstructs 108 a CT image of the ROI by applying the DFOV of the ROI to a portion of the pre-processed projection data that represents the ROI and reconstructs 110 a CT image of the remaining portion of the object 74 by applying the DFOV of the object to another portion of the pre-processed projection data that represents the remaining portion of the object 74. For example, image reconstructor 34 reconstructs a single CT image including the ROI by applying the DFOV of the ROI to a portion of the pre-processed projection data that represents the ROI and reconstructs the single CT image including the remaining portion of the object 74 by applying the DFOV of the object to another portion of the pre-processed projection data that represents the remaining portion of the object 74.

Figure 5:
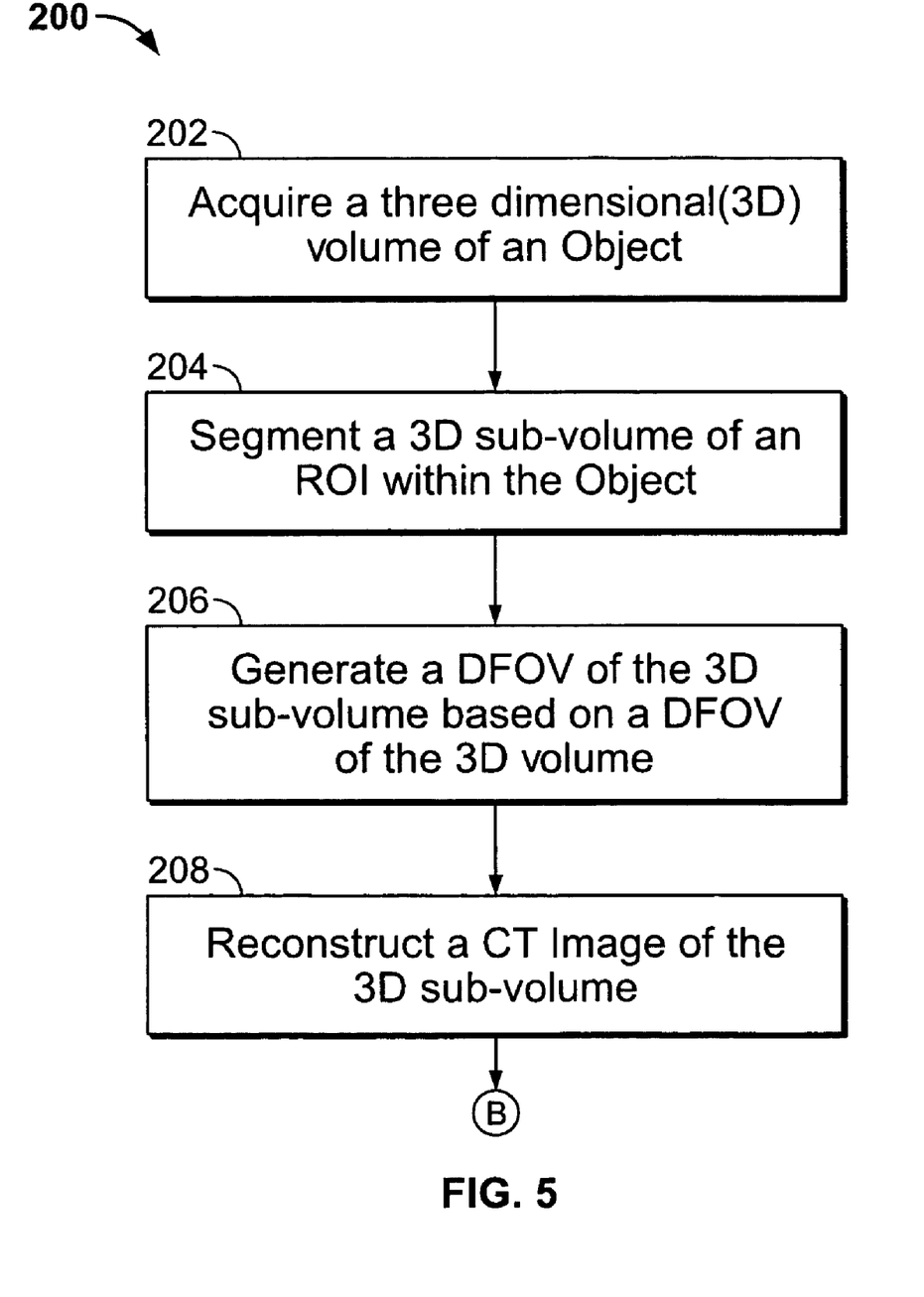
FIG. 5 is a flowchart of an alternative embodiment of a method for improving a resolution of an image.
Figure 6:
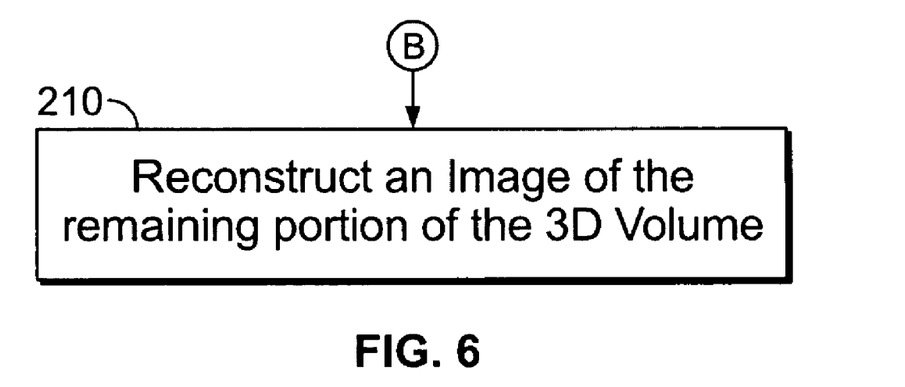
FIG. 6 is a continuation of the flowchart of FIG. 5.

FIGS. 5 and 6 is a flowchart of an embodiment of a method 200 for improving a resolution of an image. Method 200 is executed by computer 64 and image reconstructor 34. In an alternative embodiment, method 200 is performed by a single controller. Computer 64 acquires 202 a three-dimensional (3D) volume of the object 74. As an example, the 3D volume is generated by producing helical projection data. In the example, the helical projection data is produced by performing a helical scan. As another example, the 3D volume is generated by performing a plurality, such as two or three, axial scans of the object 74 and by combining, such as integrating along the z-axis, axial projection data from the axial scans. The axial projection data from the axial scans can be combined after magnifying the axial projection data from one of the axial scans to the same value as that of the axial projection data from the remaining of the axial scans and by rotating one of the axial projection data from one of the axial scans to the same view or gantry angle as that of the axial projection from the remaining of the axial scans. Computer 64 acquires the 3D volume having a high spatial resolution, such as ranging from and including 0.2 mm to 0.5 mm by receiving the DFOV of the object 74 having the low value ranging from and including 10 cms to 20 cms. Alternatively, computer 64 acquires the 3D volume having a low spatial resolution, such as ranging from and including 0.4 mm to 0.8 mm, by receiving the DFOV of the object 74 having the high value ranging from and including 20 cms to 40 cms.

Computer 64 executes an analysis algorithm to segment 204 a 3D sub-volume of the ROI from the remaining portion of the 3D volume. As an example, computer 64 receives a bone profile that is pre-stored by the user via console 40 into mass storage device 38 and a vertebral artery profile also pre-stored by the user via console 40 into mass storage device 38. Computer 64 distinguishes a vertebral artery having the vertebral artery profile from a bone having the bone profile. As another example, computer 64 receives a location, a shape, and/or a structure of the 3D sub-volume and distinguishes the 3D sub-volume from the remaining portion of the 3D volume. The remaining portion of the 3D volume excludes the 3D sub-volume. In an alternative embodiment, the user manually distinguishes the 3D sub-volume from the remaining portion of the 3D volume by selecting, via console 40, the 3D sub-volume. The user selects the 3D sub-volume by marking the 3D sub-volume with a marking tool, such as, a cube or an ellipsoid on display 42.

Computer 64 generates 206 a DFOV of the 3D sub-volume based on the DFOV of the 3D volume. As an example, upon determining that the DFOV of the 3D volume has the low value, computer 64 generates the high value as the DFOV of the 3D sub-volume. On the other hand, upon determining that the DFOV of the 3D volume has the high value, Computer 64 generates the low value as the DFOV of the 3D sub-volume.

Computer 64 transmits the DFOVs of the 3D sub-volume and the 3D volume to image reconstructor 34. CT imaging system 10 performs a scan of the object 74 to generate the pre-processed projection data. Image reconstructor 34 receives the pre-processed projection data of the object 74 from pre-processor. Image reconstructs reconstructs 208 a CT image of the 3D sub-volume by applying the DFOV of the 3D sub-volume to a portion of the pre-processed projection data that represents the 3D sub-volume and reconstructs 210 an image of the remaining portion of the 3D volume by applying the DFOV of the 3D volume to another portion of the pre-processed projection data that represents the remaining portion of the 3D volume. For example, image reconstructor 34 reconstructs a single CT image including the 3D sub-volume by applying the DFOV of the 3D sub-volume to a portion of the pre-processed projection data that represents the 3D sub-volume and reconstructs the single CT image including the remaining portion of the 3D volume by applying the DFOV of the 3D volume to another portion of the pre-processed projection data that represents the remaining portion of the 3D volume.

It is noted that the methods can be applied to other imaging systems, such as, a positron emission tomography (PET) imaging system, a CT-PET imaging system, a magnetic resonance imaging (MRI) imaging system, or an ultrasound imaging system. Examples of the CT-PET imaging system include a Discovery LS PET-CT system commercially available from General Electric™ Medical Systems, Waukesha, Wisconsin. Another example of the CT-PET imaging system includes a Discovery ST system commercially available from General Electric™ Medical Systems. Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

Technical effects of the herein described systems and methods for improving a resolution of an image include reducing a dose to subject 16 and increasing a speed of reconstruction. The dose is reduced because quality of an image reconstructed is quickly improved. Other technical effects include improving processing time by downsampling from a high resolution to a low resolution on demand by the user.

While the invention has been described in terms of various specific embodiments, those skilled in the art will recognize that the invention can be practiced with modification within the spirit and scope of the claims.

What is claimed is:

1. A method for improving a resolution of an image, said method comprising:

generating first projection data by performing a first scan of an object and by receiving a display field-of-view of the object, the first projection data including a first resolution;

generating a second resolution using the first projection data and the first resolution from the first scan;

generating pre-processed projection data by separately scanning performing a second scan of the object;

reconstructing an image of a first portion of the object by applying the first resolution from the first scan to a portion of the pre-processed projection data from the second scan that corresponds to the first portion;

reconstructing an image of a second portion of the object by applying the second resolution generated using the first scan to a portion of the pre-processed projection data from the second scan that corresponds to the second portion; and displaying a reconstructed image for viewing by a user, the reconstructed image includes the first portion of the object reconstructed at the first resolution and the second portion of the object reconstructed at the second resolution.

2. A method in accordance with claim 1 wherein displaying a reconstructed image further comprises displaying a three-dimensional image for viewing by a user.

3. A method in accordance with claim 1 further comprising generating the second resolution based on the first resolution by generating the second resolution higher than the first resolution.

4. A method in accordance with claim 1 further comprising segmenting the second portion from the first portion.

5. A method in accordance with claim 1 wherein the second portion comprises a region of interest within the object.

6. A method in accordance with claim 1 further comprising segmenting the second portion from the first portion by segmenting the second portion within the first projection data representing the object.

7. A method in accordance with claim 1 further comprising segmenting the second portion from the first portion by segmenting a three-dimensional volume representing the object.

8. A method in accordance with claim 1 further comprising segmenting the second portion from the first portion by automatically segmenting, by a controller, the second portion from the first portion.

9. A method in accordance with claim 1 further comprising segmenting the second portion from the first portion by segmenting the second portion within data acquired by a helical scan of the object.

10. A method in accordance with claim 1 further comprising manually segmenting the second portion from the first portion.

11. A method in accordance with claim I further comprising generating the second resolution based on the first resolution by generating the second resolution lower than the first resolution.

12. A controller configured to:

generate first projection data by performing a first scan of an object and by receiving a display field-of-view of the object, the first projection data including a first resolution;

generate a second resolution using the first projection data and the first resolution from the first scan; generate pre-processed projection data by performing a second scan of the object;

reconstruct an image of the object by applying the first resolution from the first scan to a portion of the pre-processed projection data from the second scan that corresponds to a first portion of the object;

reconstruct an image of the object by applying the second resolution generated using the first scan to a portion of the pre-processed projection data from the second scan that corresponds to a second portion of the object; and display a reconstructed image for viewing by a user, the reconstructed image includes the first portion of the object reconstructed at the first resolution and the second portion of the object reconstructed at the second resolution.

13. A controller in accordance with claim 12 further configured to display a three-dimensional image for viewing by a user.

14. A controller in accordance with claim 12 further configured to generate the second resolution based on the first resolution by one of:

generating the second resolution higher than the first resolution; and generating the second resolution lower than the first resolution.

15. A controller in accordance with claim 12 further configured to segment the second portion from the first portion.

16. A controller in accordance with claim 12 wherein the second portion comprises a region of interest within the object.

17. An imaging system comprising:

a source configured to generate a beam;

a detector array configured to detect the beam; and a controller configured to:

generate first projection data by performing a first scan of an object and by receiving a display field-of-view of the object, the first projection data including a first resolution;

generate a second resolution using the first projection data and the first resolution from the first scan;

generate pre-processed projection data by performing a second scan of the object;

reconstruct an image of the object by applying the first resolution from the first scan to a portion of the pre-processed projection data from the second scan that corresponds to a first portion of the object;

reconstruct an image of the object by applying the second resolution generated using the first scan to a portion of the pre-processed projection data from the second scan that corresponds to a second portion of the object; and display a reconstructed image for viewing by a user, the reconstructed image includes the first portion of the object reconstructed at the first resolution and the second portion of the object reconstructed at the second resolution.

18. An imaging system in accordance with claim 17 wherein said controller further configured to display a three-dimensional image for viewing by a user.

19. An imaging system in accordance with claim 17 wherein said controller further configured to generate the second resolution based on the first resolution by one of;

generating the second resolution higher than the first resolution; and generating the second resolution lower than the first resolution.

20. An imaging system in accordance with claim 17 wherein said controller further configured to segment the second portion from the first portion.

* * * * *